United States Patent
Donnan

[11] Patent Number: 5,935,109
[45] Date of Patent: Aug. 10, 1999

[54] CATHETER AND NEEDLE ASSEMBLIES

[75] Inventor: Jerry Donnan, West Lothian, United Kingdom

[73] Assignee: Smiths Industries Public Limited Company, London, United Kingdom

[21] Appl. No.: 09/062,582

[22] Filed: Apr. 20, 1998

[30] Foreign Application Priority Data

Apr. 29, 1997 [GB] United Kingdom .................... 9708569

[51] Int. Cl.⁶ .................................................. A61M 5/178
[52] U.S. Cl. ........................... 604/164; 604/198; 604/110
[58] Field of Search ..................................... 604/164, 198, 604/263, 165, 110, 117, 168, 160, 161, 162, 163, 166, 167, 170, 192, 190, 235, 264

[56] References Cited

U.S. PATENT DOCUMENTS 4,944,725  7/1990  McDonald .
5,300,045  4/1994  Plassche, Jr. .
5,718,688  2/1998  Wozencroft .

FOREIGN PATENT DOCUMENTS

0545671A1  6/1993  European Pat. Off. .
0799626A1  10/1994  European Pat. Off. .
0747083A2  12/1996  European Pat. Off. .

Primary Examiner—Ronald Stright
Assistant Examiner—Kent Gring
Attorney, Agent, or Firm—Pollock, Vande Sande & Amernick

[57] ABSTRACT

A catheter assembly has a needle extending within a catheter and projecting from its patient end. A slider attached with the needle is slidable rearwardly along a protective housing so that the needle can be pulled out of the catheter into the housing. A resilient catch at the patient end of the housing has two plates with apertures through which the needle projects when extended, thereby holding two hooks on the catch in engagement with the catheter hub. The catheter cannot be pulled off the needle until the needle is pulled rearwardly of the catch and allows the hooks to release engagement with the hub.

8 Claims, 3 Drawing Sheets

CATHETER AND NEEDLE ASSEMBLIES

BACKGROUND OF THE INVENTION

This invention relates to catheter and needle assemblies.

When a catheter is inserted in a vein or similar part of the body, this is often performed using a needle inserted within the catheter. The patient end of the needle is sharp and protrudes from the patient end of the catheter. The patient end of the assembly of the catheter on the needle is inserted in the vein and the needle is subsequently removed, leaving the catheter in position. The needle may be removed through a self-sealing port at the machine end of the catheter; a separate port is used to provide fluid access to the vein. Such an assembly is described, for example, in GB 2088215.

After the needle has been removed from the catheter, its patient end will carry traces of blood, which presents a potential contamination risk to the clinician and to people subsequently handling the needle. In order to protect the tip of the needle from contact after it has been withdrawn from the catheter, it has been proposed that the needle be withdrawn into a tubular protector after use, in the manner described in EP 54671 and EP 734272. In U.S. Pat. No. 4,978,344 there is described a tethered protective cap frictionally retained in a catheter hub so that it is pulled off the catheter and retained with the needle when the needle is pulled out of the catheter hub. One problem with previous arrangements has been that it is possible for the needle to be removed from the catheter before the needle has been withdrawn into, or fully withdrawn into the protector.

BRIEF SUMMARY OF THE INVENTION

It is an object of the present invention to provide an improved catheter assembly.

According to one aspect of the present invention there is provided a catheter assembly including a catheter and a needle assembly, the catheter being open at its patient end and having at its machine end a hub with an external surface formation, the needle assembly having a needle shaft adapted to extend within the catheter with the patient end of the needle shaft projecting beyond the patient end of the catheter, the needle assembly including an elongate protective housing within which the needle shaft can be withdrawn from the catheter after use, and the housing having a catch at its patient end that engages both the surface formation on the hub of the catheter and the needle shaft such that the catch is only released from engagement with the surface formation when the patient end of the needle shaft has been withdrawn into the protective housing.

The catch preferably includes a resilient member held against one side of the hub by engagement with the opposite side of the needle shaft. The resilient member preferably includes two plates with apertures therethrough and two hooks, the needle shaft extending through the apertures of both plates and holding the hooks in engagement with the surface formation on the hub such that when the needle shaft is withdrawn through the plates the hooks are resiliently urged outwards away from the surface formation to release engagement with the hub. The resilient member may include a laterally-extending rod with a passage extending along a diameter of the rod, the needle shaft extending through the passage. The resilient member may be retained within one end of the housing divided into a plurality of axially-extending prongs. The assembly is preferably arranged to prevent forward displacement of the needle assembly once the needle shaft has been withdrawn into the housing. The catch preferably prevents forward displacement of the needle assembly once the needle shaft has been withdrawn into the housing. The needle assembly may include a slider having a vent into which the machine end of the needle shaft opens, the vent sealing when wetted by fluid flowing along the needle shaft.

According to another aspect of the present invention there is provided a needle assembly for a catheter assembly according to the above one aspect of the invention.

According to a further aspect of the present invention there is provided a needle assembly for use with a catheter, said needle assembly including a needle shaft, an elongate protective housing, a slider mounted with the machine end of the needle shaft and slidable along the housing from a first position in which the patient end of the shaft protrudes from the housing to a second position in which the patient end of the shaft is protected within the housing, and a catch located at the patient end of the housing, the catch being arranged to engage the needle shaft when the slider is in the first position and to disengage the shaft when the slider is in the second position, and the catch being arranged to retain the catheter with the needle assembly when the catch engages the needle shaft and to release the catheter from the needle assembly when the catch disengages the needle shaft.

A venous catheter assembly in accordance with the present invention will now be described, by way of example, with reference to the accompanying drawings.

DETAILED DESCRIPTION OF THE PREFERRED EMBODIMENT

Figure 1:
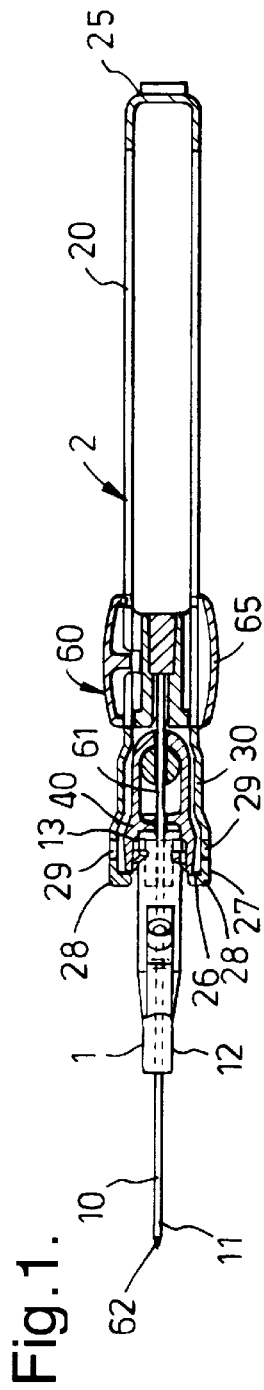
FIG. 1 is a sectional plan view of the assembly with the needle assembly connected with the catheter.
Figure 2:
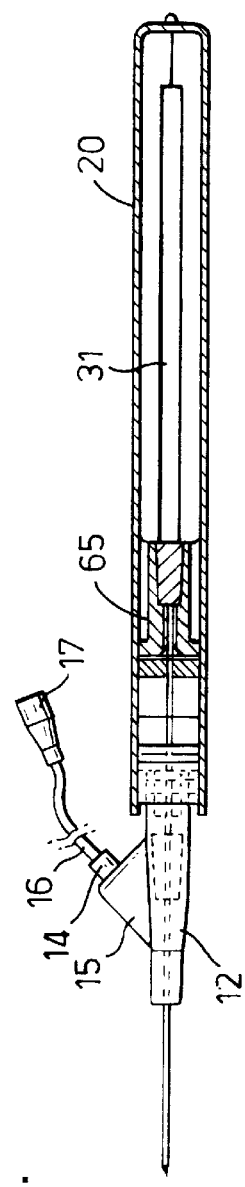
FIG. 2 is a sectional side elevation view of the assembly of FIG. 1.
Figure 3:
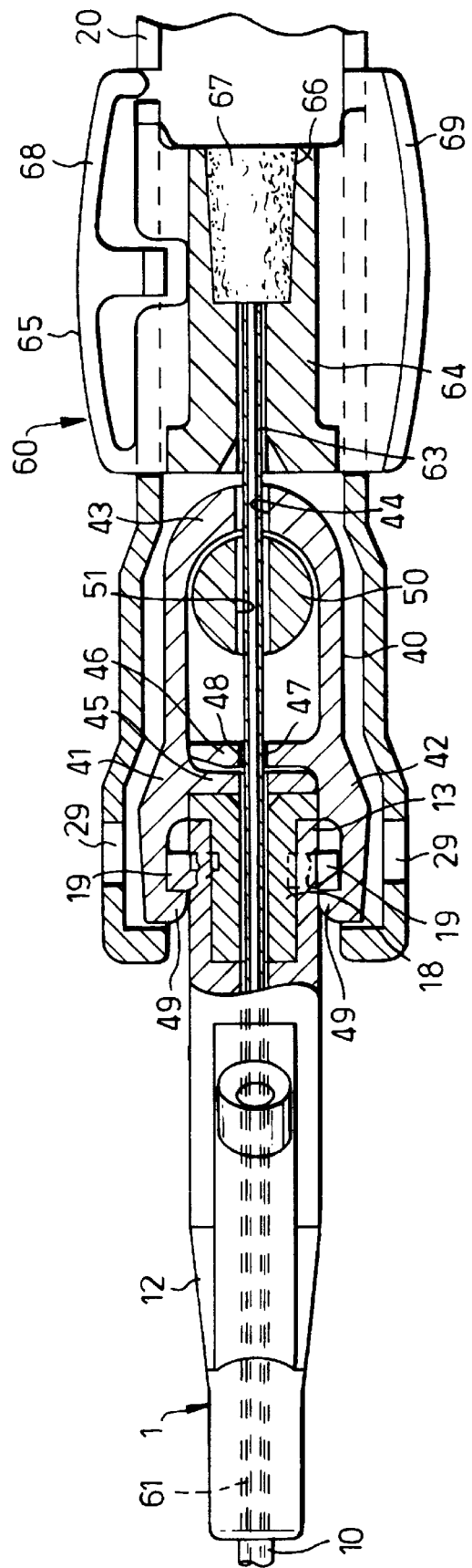
FIG. 3 is a sectional plan view of a part of the assembly to an enlarged scale.

With reference to FIGS. 1 to 3, the assembly comprises a catheter 1 and a needle assembly 2. The needle assembly is used to introduce the catheter into a vein and is subsequently removed and discarded.

The catheter 1 is a conventional venous catheter, such as sold by SIMS Portex Limited under the trade mark Y-Can. The catheter 1 has a flexible tubular shaft 10 with an open patient end 11. The machine end of the shaft 10 is secured in a rigid, plastics hub 12, which has a machine end port 13 aligned axially with the shaft, and a side port 14 on a wing member 15. A small-bore flexible tube 16 is bonded to the side port 14 and extends away from the hub at an angle of about 45 degrees. The tube 16 is terminated by a connector 17. Both the bore in the tube 16 and the port 13 communicate with the passage through the catheter shaft 10, but the port 13 contains a self-sealing septum 18, which seals closed after withdrawal of the needle. Externally, the hub 12 has two wedge-shape projections 19 arranged diametrically opposite one another around the machine end port 13, which provide a screw-thread for securing a cap, or other luer-compatible device, to the port after removal of the needle assembly. Instead of these projections, alternative surface formations could be provided.

The needle assembly 2 comprises an outer elongate protective housing 20, a catch 40 located at the patient end of the housing to engage the hub 12 of the catheter 1, and a needle member 60 slidable along the housing.

The housing 20 is moulded from a rigid, transparent plastics material, such as modified styrene and is about 105 mm long and about 10 mm square in section along most of its length. The rear, machine end 25 of the housing is closed. The forward, patient end 26 of the housing 20 is open. At its open end 26, the housing 20 is increased in width along two regions. In the first region 27, at the forward end of the housing, it is divided into three axially-extending prongs 28 equally spaced around the housing, the width of the housing across the prongs being about 14 mm. Each prong 28 has a small aperture 29 through it for assembly purposes. This forward region 27 connects with an adjacent region 30 where the housing 20 is continuous around its periphery and which has a width of about 12 mm. The height of the housing 20 is the same along its entire length. The housing 20 has two slots 31 extending axially on opposite sides and terminating just short of the forward and rear ends of the housing.

The catch 40 is located in the enlarged regions 27 and 30 at the forward end of the housing 20 and is moulded from a stiff, resilient plastics material, such as polypropylene. The catch 40 is a relatively loose fit within the housing 20 but the fit is such as to ensure that it cannot be slid rearwardly along the housing. The catch 40 has two arms 41 and 42 connected at their rear end by a curved spring portion 43, which has a central aperture 44. About half way along their length, each arm 41 and 42 has a shutter plate 45 and 46 respectively projecting laterally inwardly side-by-side between the two arms. Each plate 45 and 46 has a central aperture 47 and 48, the resilience of the catch being such that, an inwardly directed force must be applied to deflect the two shutter plates 45 and 46 inwards sufficiently for the apertures to align with one another. At their forward ends, the arms 41 and 42 have inwardly-directed hooks 49 shaped to engage with the projections 19 on the catheter hub 12. The catch 40 also includes a laterally-extending rod 50 of circular section with a passage 51 therethrough extending along a diameter. The rod 50 is located between the curved spring portion 43 and the shutter plates 45 and 46.

The needle member 60 has a hollow metal needle shaft 61 with a sharply pointed, chamfered patient end 62, the length of the needle member being such that its patient end just projects beyond the patient end 11 of the catheter shaft 10. The rear machine end 63 of the shaft 61 is mounted in the central body portion 64 of a slider 65 moulded from a transparent plastics material, such as ABS. The rear end 63 of the needle shaft 61 abuts the forward end of a hydrophobic vent plug 66 secured in an open recess 67 at the rear end of the body portion 64. The body portion 64 of the slider 65 is a loose fit within the housing 20 so that it can be slid freely along its length. The slider 65 has two finger grips 68 and 69 projecting laterally outwardly from opposite sides of the body portion 64, through the slots 31 so that the grips can be accessed externally.

The catheter assembly is supplied in the condition shown in FIGS. 1 to 3. The slider 65 of the needle member 60 is located at the forward end of the housing 20 and the needle shaft 61 extends along the bore of the shaft 10 of the catheter 1, with its patient end 62 just projecting from the patient end 11 of the catheter. The needle shaft 61 projects through the catch 40 and, more particularly, it projects through the aperture 44 in the curved portion 43, the passage 51 through the rod 50 and the apertures 47 and 48 in the shutter plates 45 and 46. The needle shaft 61 retains the shutter plates 45 and 46 with their apertures 47 and 48 in alignment, against the resilience of the two arms 41 and 42 and the curved portion 43. The needle shaft 61 is engaged by the sides of the apertures 47 and 48 further from their respective arms 41 and 42.

Figure 6:
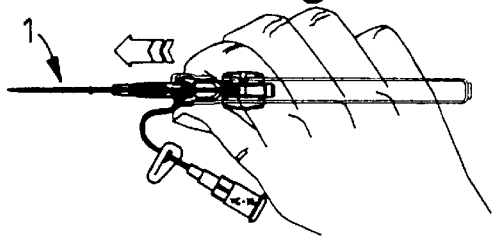
FIGS. 6 to 10 are plan views illustrating different steps in use of the assembly.

In use, the assembly is gripped at the forward end of the housing 20 and the forward end 62 of the needle shaft 61 and catheter 10 is pushed into a vein, in the usual way, as shown in FIG. 6. When venepuncture has been achieved, blood flows along the bore of the needle shaft 61, air in the needle being expelled through the hydrophobic vent 66. When blood reaches this vent 66, the hydrophobic material absorbs the blood and turns red, which color change is visible to the user through the slider 65 and housing 20. When the vent 66 is wetted, it seals to prevent escape of blood.

Figure 4:
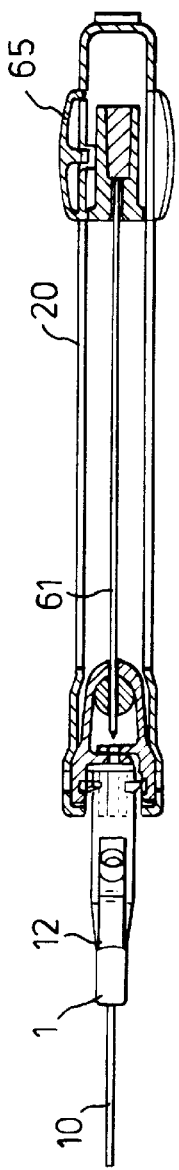
FIG. 4 is a sectional plan view of the assembly with the needle assembly withdrawn from the catheter.
Figure 5:
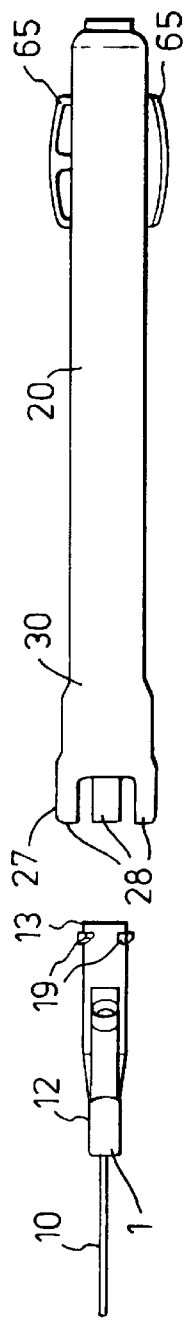
FIG. 5 is a plan view of the assembly with the needle assembly separated from the catheter.
Figure 7:
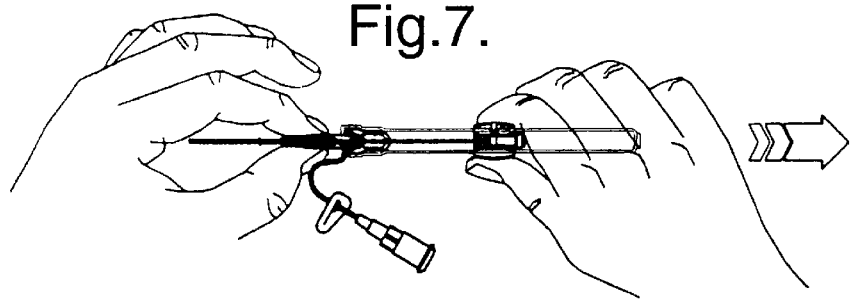
Figure 8:
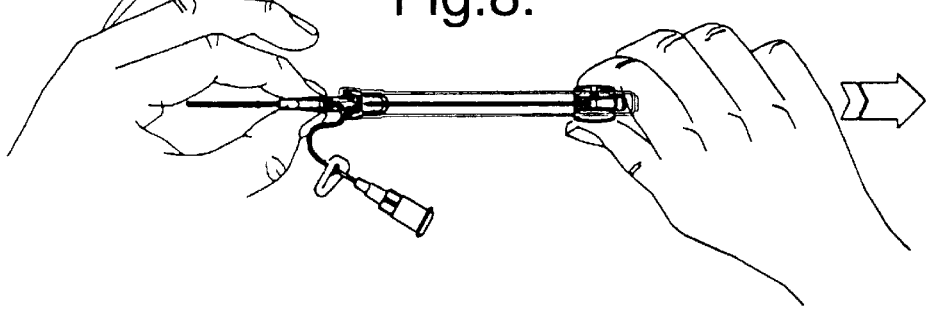
Figure 9:
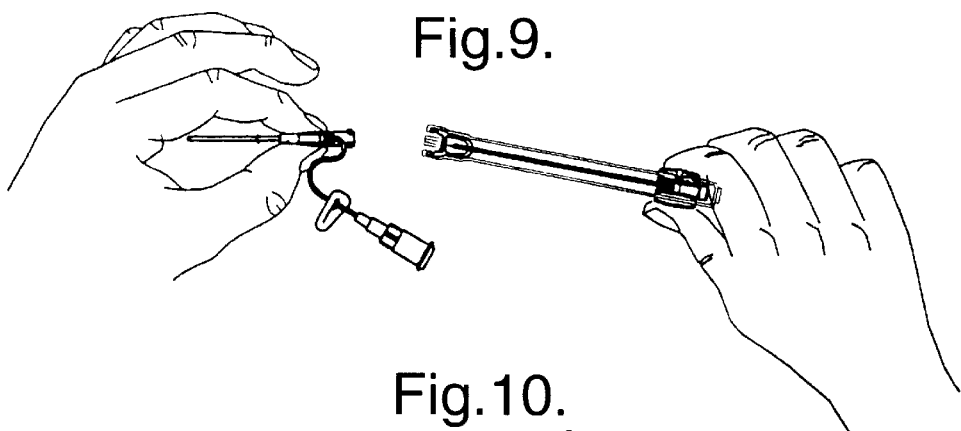
Figure 10:
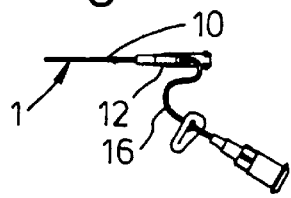

The user then holds the hub 12 of the catheter 1 with one hand and holds the grips 68 and 69 of the slider 65 between the finger and thumb of the other hand. He pulls the slider 65 rearwardly along the housing 20 so that the needle shaft 61 is withdrawn from the shaft 10 of the catheter 1, as shown in FIG. 7. The housing 20 remains securely attached to the catheter hub 12 during this process. As the tip 62 of the needle shaft 61 is pulled out of the hub 12 of the catheter 1, its self-sealing septum 18 prevents flow of blood out of the hub. When the slider 65 is pulled back to its full extent along the housing 20, as shown in FIGS. 4 and 8, the patient end of the needle is withdrawn through the apertures 47 and 48 of the shutter plates 45 and 46, allowing the arms 41 and 42 to spring outwardly under their natural resilience. The hooks 49 are disengaged from the projections 19 on the catheter hub 12 and the needle assembly 2 is released from the catheter 1, as shown in FIGS. 5 and 9. The catheter 1 remains in position in the patient, as shown in FIG. 10. Its hub 12 is preferably closed with a cap screw threaded onto the projections 19, and the tube 16 is used to make access to the vein.

The patient end 62 of the needle shaft 61 is located within the catch 40, extending through the rod 50 but being located rearwardly of the shutter plates 45 and 46. Because the apertures 47 and 48 in the shutter plates 45 and 46 are out of alignment with one another, any forward movement of the needle shaft 61 will bring its point into contact with the rear shutter plate 46 and prevent further displacement, The needle shaft 61 is, therefore, safely locked within the housing 20 and cannot be exposed or re-used. Because the housing 20 cannot be removed from the catheter 1 until the needle shaft 61 is fully enclosed within the housing, there is no risk of accidental needle prick and contamination.

Various modifications are possible to the assembly. For example, instead of using shutter plates to prevent forward movement of the needle after withdrawal, this could be done by some form of engaging formations on the housing and slider. The catch could take various different forms, apart from shutter plates with apertures, where the catch engages both surface formations on the catheter hub and the shaft of the needle and releases engagement of the surface formations when the needle has been withdrawn into the housing.

It will be appreciated that the invention is not confined to venous catheter assemblies but could be used with other catheter assemblies where a needle or similar sharp device extends along the catheter for introducing the catheter.

What I claim is:

1. A catheter assembly comprising: a catheter, said catheter having a machine end and a patient end; and a needle assembly, said needle assembly including a needle shaft, said needle shaft having a patient end and a machine end, wherein said catheter is open at its said patient end and has a hub at its said machine end, said hub having an external surface formation, wherein said needle shaft is slidable within said catheter with the said patient end of said needle shaft projecting beyond the said patient end of said catheter, wherein said needle assembly includes an elongate protective housing, wherein said needle shaft is slidable into said housing from said catheter after use, wherein said housing has a catch at a patient end of said housing that is engageable with both the said surface formation on the said hub and with said needle shaft such that said catch is only released from engagement with said surface formation when the said patient end of said needle shaft has been withdrawn into said protective housing, and wherein said catch blocks extension of said needle shaft from said housing when said catch is released from engagement with said surface formation.

2. A catheter assembly according to claim 1, wherein said catch includes a resilient member held against one side of said hub by engagement with an opposite side of said needle shaft.

3. A catheter assembly according to claim 2, wherein the said resilient member includes two hooks and two plates, said plates each having an aperture therethrough, and wherein said needle shaft extends through the said apertures of both said plates and thereby holds said hooks in engagement with said surface formation on said hub.

4. A catheter assembly according to claim 2, wherein one end of said housing is divided into a plurality of axially-extending prongs, and wherein said resilient member is retained within the said one end of said housing.

5. A catheter assembly comprising: a catheter, said catheter having a machine end and a patient end; and a needle assembly, said needle assembly including a slider and a needle shaft, said needle shaft having a patient end and a machine end, wherein said catheter is open at its said patient end and has a hub at said machine end, wherein said needle shaft is slidable within said catheter with the said patient end of said needle shaft projecting beyond the said patient end of said catheter, wherein said needle assembly includes an elongate protective housing, wherein said needle shaft is slidable into said housing from said catheter after use by engagement with said slider, and wherein said housing has a catch at a patient end of said housing, said catch having a spring arm that engages one side of said hub and an opposite side of said needle shaft such that said catch is only released from engagement with said hub when the said patient end of said needle shaft is located rearwardly of said catch in said protective housing.

6. A needle assembly for use with a catheter, said needle assembly comprising: a needle shaft, said needle shaft having a patient end and a machine end; an elongate protective housing; a slider, said slider being mounted with said machine end of said needle shaft and being slidable along said housing from a first position in which the said patient end of said shaft protrudes from said housing to a second position in which the said patient end of said shaft is protected within said housing; and a catch, said catch being located at a patient end of said housing, said catch engaging said needle shaft when said slider is in said first position and disengaging said shaft when said slider is in said second position, and said catch being operable to retain said catheter with said needle assembly when said catch engages said needle shaft and to release said catheter from said needle assembly when said catch disengages said needle shaft.

7. A catheter assembly comprising: a catheter having a machine end and a patient end; and a needle assembly which includes a needle shaft having a patient end and a machine end, said catheter being open at its said patient end and having a hub at its said machine end, said hub having an external surface formation, said needle shaft being slidable within said catheter with the said patient end of said needle shaft projecting beyond the said patient end of said catheter, said needle assembly including an elongate protective housing, said needle shaft being slidable into said housing from said catheter after use, said housing having a catch at a patient end of said housing that is engageable with both the said surface formation on the said hub and with said needle shaft such that said catch is only released from engagement with said surface formation when the said patient end of said needle shaft has been withdrawn into said protective housing, said catch including resilient member held against one side of said hub by engagement with an opposite side of said needle shaft, said resilient member including a laterally-extending rod with a passage extending along a diameter of said rod, and said needle shaft extending through said passage.

8. A catheter assembly comprising: a catheter having a machine end and a patient end; and a needle assembly which includes a needle shaft having a patient end and a machine end, said catheter being open at its said patient end and having a hub at its said machine end, said hub having an external surface formation, said needle shaft being slidable within said catheter with the said patient end of said needle shaft projecting beyond the said patient end of said catheter, said needle assembly including an elongate protective housing, said needle shaft being slidable into said housing from said catheter after use, said needle assembly including a slider having a vent into which said machine end of said needle shaft opens, said vent being sealed when wetted by fluid flowing along said needle shaft, and said housing having a catch at a patient end of said housing that is engageable with both the said surface formation on the said hub and with said needle shaft such that said catch is only released from engagement with said surface formation when the said patient end of said needle shaft has been withdrawn into said protective housing.

\* \* \* \* \*